US00PP13873P39

(12) United States Plant Patent
Pieters

(10) Patent No.: US PP13,873 P3
(45) Date of Patent: Jun. 10, 2003

(54) CHRYSANTHEMUM PLANT NAMED 'GEDI ONE IBE'

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 09/873,876

(22) Filed: Jun. 4, 2001

(65) Prior Publication Data

US 2002/0184686 P1 Dec. 5, 2002

(51) Int. Cl.[7] ..... A01H 5/00
(52) U.S. Cl. ..... Plt./288
(58) Field of Search ..... Plt./294, 286, 287, Plt./288

(56) References Cited

U.S. PATENT DOCUMENTS

PP11,637 P 11/2000 Noodelijk

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a decorative type inflorescence, consistent flowering response to short days, blooming consistently after 49 days of short day length, free branching habit, white ray florets, very uniform round growth habit, and a large quantity of blooms per flowering branch.

1 Drawing Sheet

LATIN NAME

*Dendranthema morifolium.*

VARIETY

Figure 1:
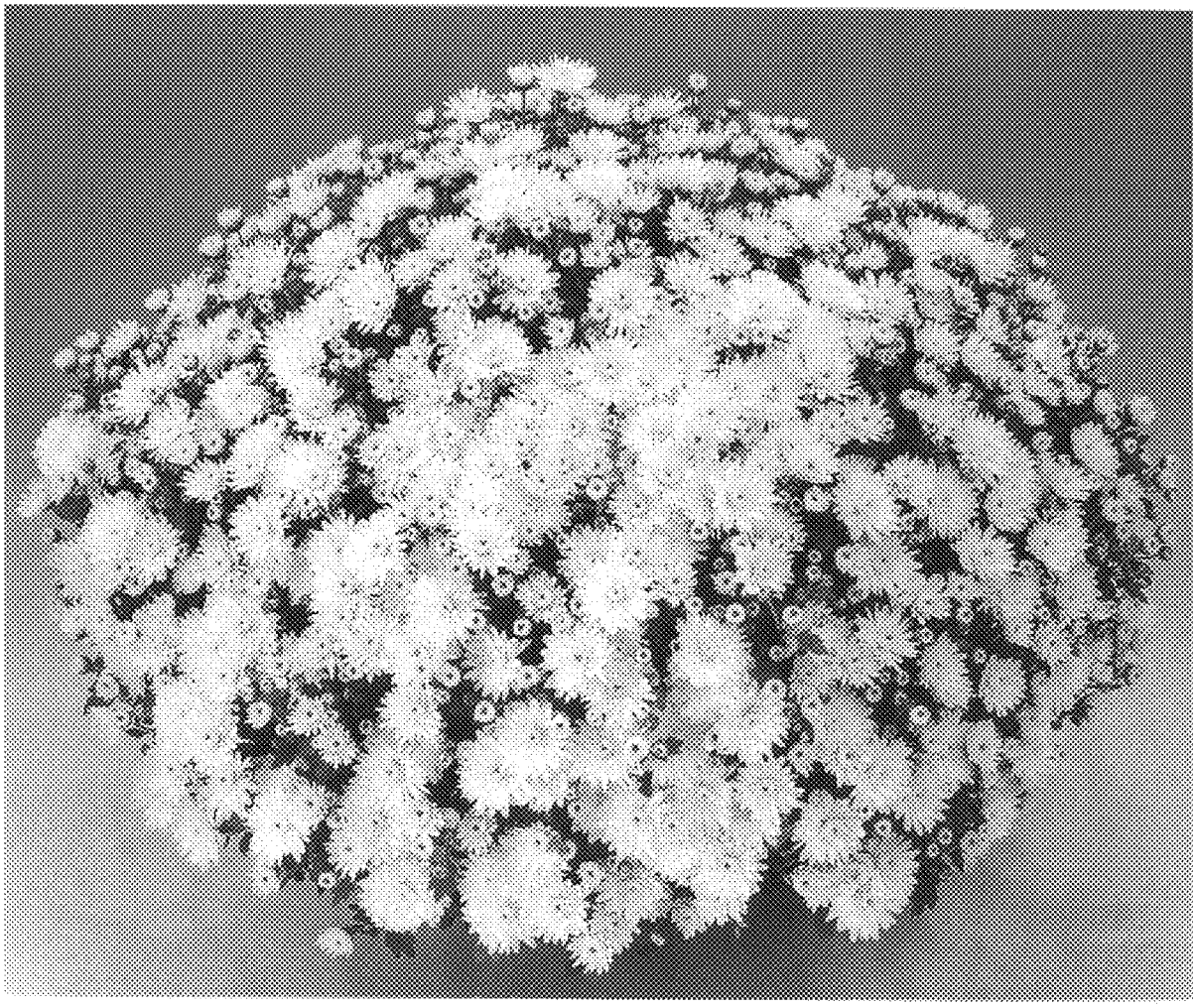

'GEDI ONE IBE'.

BACKGROUND OF THE INVENTION

The present invention relates to a new and distinct cultivar of Chrysanthemum plant, herein after referred to by the cultivar name 'GEDI ONE IBE'.

This new cultivar originated from hybridization of a female parent, cultivar 'Cassablanco' (unpatented in the United States), and a male parent cultivar 'Papiro' (U.S. Plant Pat. No. 12,998). The new cultivar was discovered by the inventor in October 1997.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'GEDI ONE IBE' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GEDI ONE IBE.' These characteristics in combination distinguish 'GEDI ONE IBE' as a new and distinct Chrysanthemum:

1. Decorative type inflorescence;

2. Consistent flowering response to short days, blooming consistently after 49 days of short day length;

3. Free branching habit;

4. White ray florets;

5. Very uniform round growth habit; and

6. Large quantity of blooms per flowering branch.

Plants of the new cultivar are similar to plants of the parent cultivar, 'Cassablanco,' in most horticultural characteristics, however plants of the new cultivar differed from plants of the cultivar 'Cassablanco' in the following characteristics:

1. The new cultivar has more blooms per flowering branch;

2. The new cultivar has many more ray florets; and

3. The new cultivar has a wider diameter bloom.

Plants of the new cultivar are also similar to plants of the parent cultivar, 'Papiro,' in most horticultural characteristics, however plants of the new cultivar differed from plants of the cultivar 'Papiro' in the following characteristics:

1. The new cultivar has a different flower type;

2. The new cultivar is taller and wider; and

3. The new cultivar has a wider diameter bloom.

The new cultivar can be compared to the Chrysanthemum cultivar 'Odysseus' (disclosed in U.S. Plant Pat. No. 11,637). However plants of the new Chrysanthemum differed from the plants of the cultivar 'Odysseus' in the following characteristics:

1. The new cultivar naturally blooms 2 weeks later;

2. The new cultivar has a more flexible plant habit;

3. The new cultivar has a more round plant shape and greater branching; and

4. The new cultivar has more blooms per flowering branch.

BRIEF DESCRIPTION OF THE PHOTOGRAPHS

The photograph shows a plant of 'GEDI ONE IBE' grown in a 2-gallon container. A single cutting was used in the pot, planted mid-May and grown under outdoor field conditions.

DETAILED BOTANICAL DESCRIPTION

In the following description, color references are made to The Royal Horticultural Society Colour Chart except where general terms of ordinary dictionary significance are used. The following observations and measurements describe plants grown in a commercial field in Oxnard, Calif. in the month of September 2000, 125 days from rooted cuttings. The growing conditions range from 60° to 65° F. at night to 70° to 85° F. during the day. Measurements and numerical values represent averages of typical flowering types.

Botanical classification: *Dendranthema morifolium* cultivar 'GEDI ONE IBE'.
Commercial classification: Garden-type Chrysanthemum.
Parentage: Hybridization of female parent 'Cassablanco' (unpatented in the United States) and male parent 'Papiro' (U.S. Plant Pat. No. 12,998).

PROPAGATION

Time to rooting: 7 to 14 days at approximately 21° C.
Root description: Fine, fibrous.

PLANT

Growth habit: Mounding herbaceous perennial.
Height: Approximately 29 cm.
Growth rate: Moderate.
Plant spread: Approximately 35 cm.
Branching characteristics: Free Branching.
Length of lateral branches: Approximately 24 cm.
Number of leaves per lateral branch: Approximately 23.
Stem color: Near 137A.

FOLIAGE

Leaf:
- *Arrangement.*—Alternate single.
- *Average length.*—Approximately 7.1 cm.
- *Average width.*—Approximately 4.2 cm.
- *Shape of blade.*—Ovate.
- *Apex.*—Acuminate.
- *Base.*—Attenuate.
- *Atttachment.*—Stalked.
- *Margin.*—Pinnately lobed and toothed.
- *Texture of top surface.*—Lightly pubescent.
- *Texture of bottom surface.*—Lightly pubescent.
- *Color.*—Young foliage upper side: Near 137A. Young foliage under side: Near 137A. Mature foliage upper side: Near 137A. Mature foliage under side: Near 137A. Venation upper side: Near 137C. Venation under side: Near 137C.

Petiole:
- *Average length.*—Approximately 2.5 cm.
- *Color.*—138B.
- *Diameter.*—3 mm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the last two weeks of August.
- *Number of inflorescences per stem.*—Approximately 13.
- *Inflorescence diameter.*—Approximately 7.5 cm.
- *Inflorescence depth.*—2.0 cm.
- *Inflorescence longevity on plant.*—Approximately 22–25 days.
- *Persistence.*—Persistent.

Ray florets:
- *Appearance.*—Matte.
- *Texture.*—Smooth.
- *Average number per flower.*—Approximately 300.
- *Shape.*—Oblanceolate.
- *Margin.*—Entire.
- *Apex.*—Obtuse.
- *Length.*—Approximately 4.2 cm.
- *Width.*—Approximately 1.0 cm.
- *Color.*—Upper surface at first opening: Near 13D. Upper surface at maturity: Near 155D. Upper surface at fading: Near 155D. Under surface at first opening: Near 18B. Under surface at maturity: Near 11D. Under surface at fading: Near 155D.

Disc florets:
- *Appearance.*—Shiny.
- *Texture.*—Smooth.
- *Average number per flower.*—Approximately 40.
- *Shape.*—Cylindric.
- *Apex.*—Obtuse.
- *Average length.*—Approximately 0.8 cm.
- *Average width.*—Approximately 0.2 cm.
- *Color.*—At first opening: Near 3D. At maturity: Near 3B. At fading: Near 16C.

Peduncle:
- *Length.*—At terminal end (shortest): Approximately 6 cm. At lateral end (longest): Approximately 9 cm.
- *Strength.*—Moderate.
- *Color.*—Near 137C.
- *Habit.*—Erect.
- *Surface texture.*—Lightly pubescent.

Inflorescence bud:
- *Length.*—Approximately 1.3 cm.
- *Diameter.*—Approximately 1.2 cm.
- *Form.*—Globular.
- *Color.*—Near 18D.

Phyllaries:
- *Appearance.*—Matte.
- *Texture.*—Lightly pubescent.
- *Number.*—Approximately 50 to 60.
- *Shape.*—Ovate.
- *Margin.*—Entire.
- *Apex.*—Acute.
- *Diameter.*—Approximately 0.4 cm.
- *Length.*—Approximately 0.5 cm.
- *Color.*—Upper side: Near 137B. Under side: Near 137B.

REPRODUCTIVE ORGANS

Ray florets:
- *Number of pistils per flower.*—1.
- *Stigma shape.*—2 branched.
- *Stigma color.*—Near 10B.
- *Style color.*—Near 10D.
- *Style length.*—Approximately 0.7 cm.
- *Stamens.*—Absent.

Disc florets:
- *Number of pistils per flower.*—1.
- *Stigma shape.*—Cylindric.

*Style length.*—Approximately 0.5 cm.
*Number of stamens per flower.*—Approximately 5.
*Anther shape.*—Tubular.
*Anther color.*—Near 18A.
*Pollen color.*—Near 17C.

OTHER CHARACTERISTICS

Seed production: Commercially, this plant is not used or observed in a stage wherein seeds would be produced. Therefore, seed production has not been observed to date.

Disease resistance: Neither resistance nor susceptibility to diseases and pests have been observed to date in this cultivar.

What is claimed is:

1. A new and distinct variety of Chrysanthemum plant named 'GEDI ONE IBE' as herein illustrated and described.

* * * * *